US012612588B2

(12) United States Patent
Bouras et al.

(10) Patent No.: US 12,612,588 B2
(45) Date of Patent: Apr. 28, 2026

(54) METHOD FOR CLEANING A REACTOR FOR PROCESSING A LIGNOCELLULOSIC BIOMASS

(71) Applicants: IFP Energies nouvelles, Rueil-Malmaison (FR); INSTITUT NATIONAL DE RECHERCHE POUR L'AGRICULTURE, L'ALIMENTATION ET L'ENVIRONNEMENT, Paris (FR); AGRO INDUSTRIES RECHERCHE ET DEVELOPPEMENT, Pomacle (FR)

(72) Inventors: Meriem Bouras, Rueil-Malmaison (FR); Caroline Aymard, Rueil-Malmaison (FR); Olivier Carnnot, Baccones (FR)

(73) Assignees: IFP Energies Nouvelles, Rueil-Malmaison (FR); Institut National De Recherche Pour L'Agriculture L'Alimentation Et L'Environment, Paris (FR); Argo Industries Recherche Et Developpement, Pomacle (FR)

( * ) Notice: Subject to any disclaimer, the term of this patent is extended or adjusted under 35 U.S.C. 154(b) by 613 days.

(21) Appl. No.: 17/415,829

(22) PCT Filed: Dec. 13, 2019

(86) PCT No.: PCT/EP2019/085110
§ 371 (c)(1),
(2) Date: Jun. 18, 2021

(87) PCT Pub. No.: WO2020/126918
PCT Pub. Date: Jun. 25, 2020

(65) Prior Publication Data
US 2022/0145232 A1 May 12, 2022

(30) Foreign Application Priority Data
Dec. 21, 2018 (FR) ........................................ 1873762

(51) Int. Cl.
C12M 1/00 (2006.01)
B08B 9/08 (2006.01)

(52) U.S. Cl.
CPC ............... C12M 39/00 (2013.01); B08B 9/08 (2013.01); C12M 29/20 (2013.01); C12M 45/04 (2013.01); C12M 45/06 (2013.01); C12M 45/20 (2013.01)

(58) Field of Classification Search
CPC ...... C12M 39/00; C12M 29/20; C12M 45/04; C12M 45/06; C12M 45/20; B08B 9/08;
(Continued)

(56) References Cited

U.S. PATENT DOCUMENTS 5,034,498 A * 7/1991 Himmelblau ........... C10B 49/02
527/105
9,371,488 B2 6/2016 Powell et al.
(Continued)

FOREIGN PATENT DOCUMENTS

EP 0434512 B1 10/1994
WO 15095455 A1 6/2015
(Continued)

OTHER PUBLICATIONS

Yusuf Cristi et al. "Clean-in-place systems for industrial bioreactors: Design, validation and operation" Journal for Industrial Microbiology, UK, vol. 13, No. 4, Jul. 1, 1994 (Jul. 1, 1994), pp. 201-207 DOI: 10.1007/BF01569748 ISSN: 0169-4146, XP055633871.
(Continued)

Primary Examiner — Alexander Markoff
(74) Attorney, Agent, or Firm — Millen, White, Zelano & Branigan P.C.; Ryan R. Pool

(57) ABSTRACT
The present invention relates to a processing method at acidic or neutral pH in a reactor (4) for processing ligno-
(Continued)

cellulosic biomass (P), said process including a continuous cleaning phase of the reactor which comprises introducing a basic aqueous solution (EB) into said reactor containing the biomass being processed.

12 Claims, 7 Drawing Sheets

(58) Field of Classification Search
CPC .. Y02E 50/10; C12P 7/10; C12P 19/14; C12P 2201/00; C12P 2203/00
See application file for complete search history.

(56) References Cited

U.S. PATENT DOCUMENTS

| | | | |
|---|---|---|---|
| 9,732,469 B2 | 8/2017 | Powell et al. | |
| 10,214,751 B2 | 2/2019 | Nilsen et al. | |
| 2010/0330633 A1 | 12/2010 | Walther et al. | |
| 2013/0040354 A1* | 2/2013 | Olsen | C12P 7/10 |
| | | | 435/167 |
| 2013/0236941 A1 | 9/2013 | Burns-Guydish et al. | |
| 2014/0083939 A1* | 3/2014 | Nguyen | C12M 45/03 |
| | | | 210/612 |
| 2015/0291989 A1* | 10/2015 | Kim | C12M 41/12 |
| | | | 435/99 |
| 2017/0226439 A1* | 8/2017 | Nguyen | B03B 9/06 |
| 2017/0314046 A1* | 11/2017 | Nilsen | C02F 11/185 |
| 2018/0229273 A1* | 8/2018 | Carvajo Lucena | C10L 5/445 |
| 2019/0241984 A1 | 8/2019 | Hudebine et al. | |

FOREIGN PATENT DOCUMENTS

| | | | | |
|---|---|---|---|---|
| WO | WO-2016004482 A1 * | 1/2016 | .............. | D21C 1/04 |
| WO | 16066752 A1 | 5/2016 | | |
| WO | WO-2016066752 A1 * | 5/2016 | .............. | C12P 7/10 |
| WO | WO-2017093526 A1 * | 6/2017 | ........... | C12M 21/12 |
| WO | 18015227 A1 | 1/2018 | | |
| WO | WO 2018/015227 * | 1/2018 | | |

OTHER PUBLICATIONS

Hebel et al. "Making Glass Bioreactors CIP and SIP Capable", vol. 34, No. 16, Sep. 15, 2014 (2014-09-15), pp. 34-35, Genetic Engineering News, Retrieved from the Internet: http://www.genengnews.com/issue/past DOI: 10.1089/GEN.34.16.15 ISSN: 0270-6377, XP009516741.

Bill Miley et al. "Large-Scale Fermentation Systems: Hygienic Design Principles" Chemical Engineering. Engineering Practice, Nov. 1, 2015 (Nov. 1, 2015), pp. 59-65, Retrieved from the Internet: https://www.chemengonline.com/large-scale-fermentation-systems-hygienic-design-principles/ [retrieved on Oct. 18, 2019] XP055633878.

David J. Walker et al. "Process Optimization of Steam Explosion Parameters on Multiple Lignocellulosic Biomass Using Taguchi Method—A Critical Appraisal" Frontiers in Energy Research, vol. 6, Jun. 1, 2018 (Jun. 1, 2018), pp. 1-13 DOI: 10.3389/fenrg.2018.00046 XP055633882.

International Search Report PCT/EP2019/085110 dated Mar. 25, 2020 (pp. 1-3).

* cited by examiner

METHOD FOR CLEANING A REACTOR FOR PROCESSING A LIGNOCELLULOSIC BIOMASS

TECHNICAL FIELD

The invention relates to a process for the treatment of lignocellulosic biomass to produce "second generation" ("2G") sugary juices. These sugary juices can be used to produce other products by a biochemical route (for example alcohols, such as ethanol, butanol or other molecules, or solvents, such as acetone, and the like). This process comprises different stages, generally three stages of which are the preparation of liquor, the impregnation of the biomass with this liquor, and the pretreatment of the impregnated biomass by cooking, in particular with steam explosion.

PRIOR ART

Lignocellulosic biomass represents one of the most abundant renewable resources on Earth. The substrates considered are very varied; they concern both ligneous substrates, such as various woods (hardwoods and softwoods), and coproducts resulting from agriculture (wheat straw, corn cobs, and the like) or from other food-processing, paper, and the like, industries. The process for the biochemical transformation of the lignocellulosic material into 2G sugary juices comprises in particular a pretreatment stage and a stage of enzymatic hydrolysis by an enzymatic cocktail. These processes also generally comprise an impregnation stage before the pretreatment. The sugary juices resulting from the hydrolysis are subsequently treated, for example by fermentation, and the process can also comprise stages of separation and/or a stage of purification of the final product.

Lignocellulosic biomass is composed of three main polymers: cellulose (35% to 50%), which is a polysaccharide essentially consisting of hexoses; hemicellulose (20% to 30%), which is a polysaccharide essentially consisting of pentoses; and lignin (15% to 25%), which is a polymer of complex structure and of high molecular weight, composed of aromatic alcohols connected by ether bonds. These various molecules are responsible for the intrinsic properties of the plant wall and are organized in a complex entanglement.

Among the three base polymers which lignocellulosic biomass incorporates, cellulose and hemicellulose are those which make possible the production of 2G sugary juices.

Most often, hemicellulose is predominantly broken down into monomeric and oligomeric sugars during the pretreatment, and cellulose is converted into glucose by enzymatic hydrolysis. However, access to crude cellulose in the native substrate remains difficult for enzymes to access, hence the need for a pretreatment. This pretreatment makes it possible to modify the physicochemical properties of the lignocellulosic material in order to improve the accessibility of the cellulose to enzymes and its reactivity to enzymatic hydrolysis.

Numerous technologies affecting the invention in order to carry out this pretreatment exist, which will be grouped below under the generic term of "cooking", consist in heating the biomass at high temperature for a defined period of time. Known in particular are acid cookings, where the biomass is brought into contact with an acidic solution before/during the cooking, and alkaline cookings, where the biomass is brought into contact with a basic solution before/during the cooking. Also known is "steam explosion" (acid, alkaline or impregnation-free) cooking, where the biomass is subjected to pressurized steam.

There also exist "organosolv pulping" pretreatment processes. The latter process concerns a pretreatment in the presence of one or more organic solvents and generally of water. The solvent can be an alcohol (ethanol), an acid of acetic acid or formic acid type, or also acetone, or also a mixture of these compounds. "Organosolv pulping" processes result in an at least partial dissolution of the lignin and a partial dissolution of the hemicelluloses. There are thus two outlet streams: the pretreated substrate with cellulose, hemicellulose and lignin in residual amounts, and the solvent phase which contains the dissolved lignin and a portion of the hemicelluloses. There is generally a stage of regeneration of the solvent which makes it possible to extract a lignin stream. Certain "organosolv pulping" treatments (in particular with ethanol) can be coupled with the addition of a strong acid (of the $H_2SO_4$ type). It is also possible to envisage bringing the biomass into contact with the solvent via an impregnation reactor before the cooking phase or bringing the biomass into contact with the acid catalyst before carrying out an "organosolv pulping" cooking.

Various configurations are reported, for example, in the document "Production of Bioethanol from Lignocellulosic Materials via the Biochemical Pathway: a Review", M. Balat, Energy Conversion and Management, 52 (2011), 858-875, or in the document "Bioethanol Production from Agricultural Wastes: an Overview", N. Sarkar, S. Kumar Ghosh, S. Bannerjee and K. Aikat, Renewable Energy, 37 (2012), 19-27.

One of the most effective pretreatments is the abovementioned steam explosion cooking, as it makes possible almost complete hydrolysis of hemicellulose and a significant improvement in the accessibility and the reactivity of cellulose to enzymes. This pretreatment can be preceded/followed by other treatment(s), and it is this which will more particularly affect the invention, without being limited thereto in its application, however.

It has been demonstrated that the reactors for the treatment of lignocellulosic biomass, in particular those concerning the pretreatment of biomass of by cooking type, were prone to fouling: heating the reaction medium in the reactor at high temperature results in the production of various solid residues which will adhere to the internal walls of the reactor. These residues accumulate as the operation advances, over a time which is longer than the mean residence time of the biomass in the reactor. They can gradually give rise to operating problems, such as, for example, a risk of plugging of the outlet of the reactor or increased difficulty in conveying the biomass within the reactor, and, generally, their presence negatively impacts the performance characteristics of the reactor.

A first solution provided for eliminating these residues consisted in emptying the reactor, in thus stopping it, and in opening it, in order to clean the internal walls of the reactor by mechanical and/or hydraulic action, that is to say by scraping the walls and/or by delivering water under pressure at several hundred bars. This procedure is admittedly effective but it consumes time and energy: it requires not only that the reactor be stopped but that there also be a wait for it to cool (cooking is carried out at a temperature of greater than 100° C. and under pressure), that it be opened, that cleaning be carried out, that the reactor be closed and be brought back to temperature before restarting production.

The aim of the invention is consequently to overcome these disadvantages. More specifically, an aim of the invention is to develop a process for removing all or part of these residues which is effective while reducing the reactor down-time and the spending on energy used for implementing the process.

SUMMARY OF THE INVENTION

A subject matter of the invention is first of all a process for the treatment at acidic or neutral pH in a treatment reactor of a lignocellulosic biomass, said process comprising a phase of continuous cleaning of the reactor which comprises the introduction of a basic aqueous solution into said reactor containing the biomass being treated.

In the context of the invention, the term "treatment" is understood to mean any stage targeted at modifying one characteristic at least of the biomass. It can in particular be a pretreatment, a term known in the field of the treatment of lignocellulosic biomass, having the aim of preparing it for enzymatic hydrolysis.

The pH of the basic aqueous solution before introduction into the reactor is preferably greater than or equal to 9, in particular greater than or equal to 10 or 11, and advantageously at least 12, in particular between 12.5 and 13.5.

The invention has thus developed a process for cleaning the reactor which has proved to be very effective in eliminating all, or virtually all, of the solid residue from the walls. It is thus a matter, according to the invention, of carrying out the cleaning with a basic aqueous solution (which may also be denoted subsequently by the term basic "liquor"), for example a solution containing KOH, NaOH or any other inorganic or organic base, during the actual treatment of the biomass: the cleaning is carried out while maintaining the feeding of biomass to the reactor. The cleaning of the reactor is thus carried out with a reactor at least partially filled with biomass, which was able, prior to its pretreatment in the reactor in question, to be preimpregnated with an acidic, neutral or oxidizing aqueous solution.

The cleaning according to the invention is carried out by two combined actions: it is first chemical, with the action of the basic solution which has been shown to be able to detach and/or dissolve the solid residues sticking to the internal walls of the reactor, but it is also mechanical, the biomass particles exerting an abrasive effect, in addition, on said residues.

It is a markedly simpler process to implement than a mechanical or hydraulic cleaning: this is because it can be carried out without having to open the reactor, since it is sufficient to provide inlets/outlets for basic aqueous solution (or to reuse fluid inlets/outlets already present).

It is carried out without even having to stop the production of pretreated biomass: surprisingly, this is because it has turned out that the presence of biomass has an abrasive effect, thus a positive effect with respect to the cleaning of the reactor as mentioned above, but above all it has also turned out that the biomass which is in the reactor with the basic solution does not affect the rest of the process: the treatment continues during the cleaning phase.

In addition, unlike the mechanical/hydraulic cleaning with opening of the reactor, it is not necessary to wait for the reactor to cool in order to carry out the cleaning. On the contrary, it has even turned out that carrying out the cleaning during the hot pretreatment, of the cooking type (with or without steam explosion), is very favorable to the detachment of the residues. As the reactor can remain hot during the cleaning, there is no need to reheat it, since there is no production stoppage, thus no restarting either to be planned for thermally.

Advantageously, provision can be made to heat the basic aqueous solution before its introduction into the treatment reactor, in particular to a temperature of at least 40° C., in particular of at least 80° C. and for example of at most 120° C. or 100° C. It has been found that the basic solution is effective more rapidly if it is thus preheated outside the reactor.

Advantageously again, the introduction of the basic solution into the treatment reactor can be carried out in the pretreatment reactor, the internal volume of which is at a temperature of at least 120° C., in particular of at least 140° C. It is preferably of at most 240° C. or 220° C. This internal temperature of the reactor can be that at which the pretreatment is conventionally carried out, in particular by cooking. This is because the effect of the basic solution on the solid residues stuck to the walls of the reactor is amplified when the solution/the reactor are hot.

According to one embodiment of the invention, the biomass is introduced into the treatment reactor by an introduction means with pressurization, of the conical screw conveyor type, which is washed with an aqueous solution, and this washing solution is recycled. This "pressate" can be recycled in different ways, for example as make-up water to prepare an aqueous solution of acidic or neutral pH which is optionally used, before the treatment of the biomass according to the invention, in order to impregnate it with water and/or to modify the pH thereof.

The increased water consumption of the treatment process of the invention, which is due to the use of a basic aqueous cleaning solution, is thus reduced.

Preferably, the phase of cleaning the treatment reactor with the basic solution has a duration of between 15 minutes and 8 hours, in particular between 1 and 3 hours. This duration is thus not very long and can be adjusted as a function of the frequency with which the reactor is cleaned.

Preferably, during the phase of cleaning the treatment reactor, the residence time in the reactor for treatment of the biomass impregnated with basic aqueous solution is between 5 and 15 minutes. It is thus a fairly short residence time, which is adjusted by the operating conditions of the reactor. Thus, when the biomass is conveyed from its point of entry to its point of exit in the reactor by one or more conveying screws internal to the reactor, this residence time can be adjusted by adjusting the speed of rotation of at least one of these internal conveying screws.

During the phase of cleaning the treatment reactor, the flow rate of the basic aqueous solution at the inlet of said reactor is preferably adjusted so that the solids content SC of the biomass significantly decreases during its passage through the reactor, from for example a value of 30% to 60% SC, in particular 50% SC, to a value of 15% to 25% SC, in particular 20% SC. This is because the basic aqueous solution will have a first role, which is to impregnate the biomass entering the reactor with water until the biomass is saturated with liquid.

Throughout the present text, the acronym "SC" denotes the solids content, which is measured according to the standard ASTM E1756-08(2015), "Standard Test Method for Determination of Total Solids in Biomass".

Subsequently, and this is its second role, the concentration of base (KOH for example) of the basic aqueous solution is preferably adjusted so as to increase the pH of the biomass entering the reactor from an acidic pH range of between 0.5 and 3, preferably in the vicinity of 3, to a basic pH range of between 8 and 14, preferably in the vicinity of 13. (The scenario then exists of a pretreatment of a biomass preimpregnated with an acidic liquor, and that it is thus necessary to switch to a basic pH in order to carry out the cleaning according to the invention.)

By adjusting the flow rate and the concentration of base of the solution, it is possible to saturate the biomass with water and to raise its pH, the precise amounts of basic solution consumed during a cleaning procedure naturally depending on the size of the reactor and the characteristics of the biomass entering the reactor.

Preferably, the degree of filling of the reactor with the biomass during the treatment is between 20% and 80% or 90%. During the cleaning phase, this degree of filling can be kept within this range, and even, preferably, (a little) increased (for example by reducing the rotational speed of the screw or of at least one of the internal conveying screws of the reactor when it possesses them), which tends to improve the quality of the cleaning.

The phase of continuous cleaning of the treatment reactor is carried out according to a given frequency and/or when a threshold value of a physicochemical or rheological characteristic of the reaction medium in said reactor is exceeded. This characteristic can be measured or evaluated directly or indirectly. It can, for example, be a power threshold of the motor used to rotate a conveying screw in the reactor, to rotate stirring means in the reactor or any other moving part in the latter.

According to one embodiment, it is possible to change one of the physical, chemical or rheological characteristics or the nature of the biomass feeding the treatment reactor during at least a part of its cleaning phase. This is because it can be advantageous, during the time of the cleaning, to feed the treatment reactor with a biomass with an abrasive power greater than the biomass used during the remainder of the production time. For example, it is thus possible to replace straw-type biomass during the production with poplar-type biomass during the cleaning.

Advantageously, the treatment according to the invention is a pretreatment in the sense conventional in the treatment of biomass, and this pretreatment is a cooking with steam explosion. The steam separated from the biomass in a cyclone-type separation device at the outlet of the treatment reactor can be thermally exhausted, at least in part, with the help of a heat exchanger, in order to heat the or one of the aqueous solutions used in said process. Once the heat has been extracted from the steam, the latter condenses, at least in part: the condensate can then be recovered, in particular via a condenser, and used as make-up water in the process (water for washing the various conveying screws external to the reactors, water for preparation of basic or acidic liquor, and the like).

The pretreatment can be carried out by cooking, with or without steam explosion.

According to a preferred embodiment, the biomass is impregnated with an acidic aqueous solution in an impregnation reactor, before its introduction into the pretreatment reactor. The two reactors can be mounted in series and can operate continuously.

The fact that, temporarily, the acidified biomass is brought into contact with a basic solution in the pretreatment reactor has not significantly affected the operation of the process downstream of the treatment reactor.

According to one embodiment, during at least a part of the phase of continuous cleaning of the pretreatment reactor, the acid content of the acidic aqueous solution brought into contact with the biomass during its prior impregnation in the impregnation reactor is reduced or eliminated. It is thus possible to reduce the amount of base necessary for the preparation of the basic cleaning solution, since the amount of acid contained in the biomass to be neutralized is thus lower.

According to another embodiment, during at least a part of the phase of continuous cleaning of the pretreatment reactor, the acidic aqueous solution brought into contact with the biomass, during its prior impregnation in the impregnation reactor, is replaced by a basic aqueous solution, in particular the same as that which is injected during said phase into the pretreatment reactor: it is thus possible to further reduce the consumption of base necessary for the cleaning in comparison with the preceding embodiment. It can also be replaced by an aqueous solution of neutral pH, still for the same reason.

According to an alternative form, several, in particular two, impregnation reactors are used in parallel to impregnate the biomass with an aqueous solution before its introduction into the pretreatment reactor: a first impregnation reactor is fed with acidic aqueous solution or with aqueous solution of neutral pH, and a second impregnation reactor is fed with basic aqueous solution, the two reactors operating alternately, the second reactor being operational during at least a part of the phase of cleaning the pretreatment reactor. This alternative form makes it possible to implement the preceding embodiments, by modifying the type of impregnation of the biomass before its pretreatment when the pretreatment reactor goes into cleaning mode, by switching the arrival of biomass to be impregnated from one impregnation reactor to the other.

Preferably, a separation can be carried out between biomass and aqueous phase in the liquid or vapor form at the outlet of the pretreatment reactor, by a separation device or several separation devices in parallel, in particular two separation devices, operating alternately. Items of equipment of cyclone type may be concerned.

As above for the two impregnation reactors in parallel, using several separation devices in parallel makes it possible to reduce the transition period between the production mode and the production+cleaning of the pretreatment reactor mode: with two devices in parallel, one of the two devices can be dedicated to the separation of the "basic" pretreated biomass (that pretreated during the cleaning), by separating only the biomass pretreated during the cleaning, and the other device is then dedicated to the conventional separation of the pretreated biomass with acidic or neutral impregnation (that pretreated outside the cleaning period).

The phase of cleaning the separation device(s) advantageously comprises, after the introduction of the basic aqueous solution into the pretreatment reactor, at least one rinsing of the separation device or of one of the separation devices by an aqueous solution, in particular between 1 and 10 successive rinsings. The purpose of this or these rinsings is to clean the separator from traces of "basic" biomass before returning to conventional production mode.

When several separation devices are used in parallel, operating alternately, at the outlet of the pretreatment reactor, it is possible to rinse one of the separation devices batchwise, while the other separation device(s) continue to operate and to separate the biomass at the outlet of the pretreatment reactor.

The aqueous rinsing solution can be recycled from the separation device(s), in particular that which will be dedicated to the separation of the "basic" pretreated biomass, in order to prepare the basic aqueous solution. The consumption of base of the cleaning according to the invention is thus reduced.

When the process uses only a single separation device, it is indeed rinsed but the rinsing water can be discharged from the device with the remainder of the biomass to continue the process downstream, without the need to extract it or to recycle it.

Another subject matter of the invention is a process for the treatment of lignocellulosic biomass comprising the following stages: —the preparation of an impregnation liquor containing a catalyst, in particular an acidic catalyst, —the introduction of the biomass into an impregnation reactor in order to be impregnated by the impregnation liquor, —the transfer of the impregnated biomass into a pretreatment reactor in order to undergo a pretreatment therein by cooking, —the enzymatic hydrolysis of the pretreated biomass, —the alcoholic fermentation of the enzymatic hydrolysis must obtained, such that the process is carried out continuously over all or part of said stages, and such that the impregnation reactor is cleaned without interrupting its production of pretreated biomass.

Another subject matter of the invention is a plant for the implementation of the process as described above, which plant comprises, from upstream to downstream:

a reactor for impregnation of lignocellulosic biomass in fluid connection with a vessel for preparation of an acidic aqueous solution, a reactor for pretreatment of the impregnated biomass, in fluid connection with a vessel for preparation of a basic aqueous solution, and a device for separation of the pretreated biomass downstream of the pretreatment reactor and which is associated with means for rinsing by an aqueous solution.

The implementation of the proposed invention thus simply adds, to the existing plant, a vessel for preparation of the basic solution, which can be fed with water, with concentrated base (KOH, NaOH, for example, or any other inorganic or organic base) and optionally with water/recycled basic solution. This vessel is equipped with known means for, in particular, keeping the pH of the solution constant, by addition of base (KOH) and/or of water. The vessel can also be provided with heating means for bringing the basic solution to/maintaining the basic solution at the desired temperature before introduction into the reactor. The heating means can, alternately or cumulatively, be provided on the pipe-type fluid connection means bringing the basic solution from the vessel to the reactor.

The plant in question can use two impregnation reactors and/or two separation devices and/or two pretreatment reactors, operating alternately according to whether the pretreatment reactor is or is not in the cleaning phase.

Another subject matter of the invention is any plant for the implementation of the biomass treatment process mentioned above, such that this plant comprises, successively: —an impregnation reactor fed with impregnation solution by a vessel for preparation of said solution, and with biomass, —a reactor for pretreatment of the impregnated biomass which can be fed with basic aqueous solution by a vessel for preparation of said solution, —an enzymatic hydrolysis reactor, and —an alcoholic fermentation reactor, these combined reactors being mounted in series, or at least two of them.

Another subject matter of the invention is the use of the process or of the plant described above for the treatment of biomasses of the type of wood, straw, agricultural residues, and all dedicated energy crops, in particular annual or perennial plants, such as miscanthus, in order to produce sugars, biofuels or biobased molecules.

DESCRIPTION OF THE EMBODIMENTS

The figures are very diagrammatic; the same references correspond to the same components from one figure to another. The reactors are represented in the spatial position which they substantially occupy in the operational position.

The process for cleaning a reactor for the treatment of biomass is illustrated here in the context of a process for the treatment of biomass intended to produce alcohols, in particular biofuel of the bioethanol type, according to the stages of the process according to FIG. 1 described quickly below.

It is a pretreatment, in the sense known in the field of the conversion of lignocellulosic biomass. An embodiment of this process is described in more detail, for example, in the patent WO 2018/015227, to which reference will be made if necessary.

It should be noted that the cleaning process according to the invention can be applied in the same way to any reactor for the pretreatment of biomass and more generally to any reactor which is intended to treat a lignocellulosic biomass, the treatment having the object of modifying one of its chemical, physical or rheological characteristics, and generally being operated at high temperature.

Figure 1:
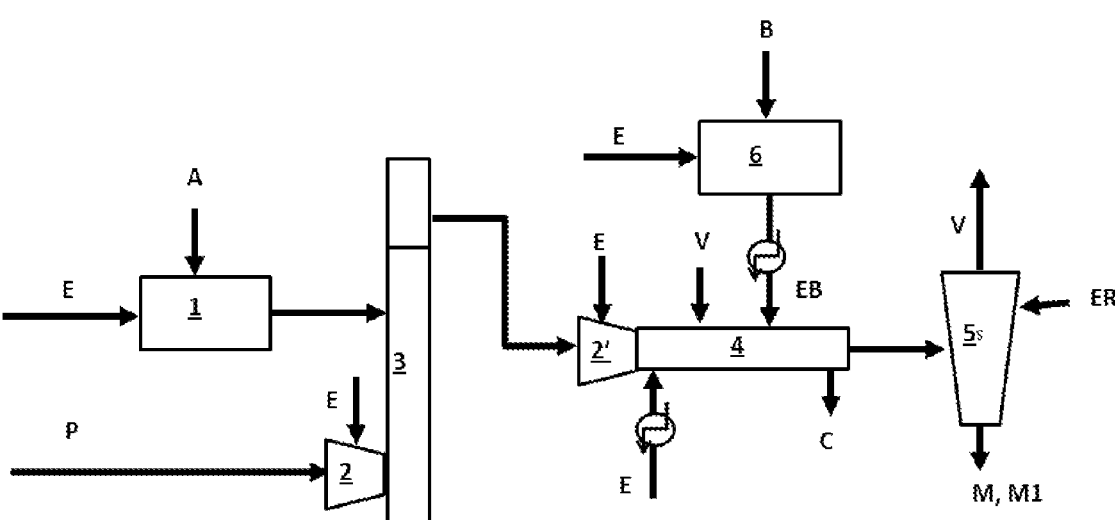
FIG. 1 represents the block diagram of the cleaning process according to the invention of a reactor for the pretreatment of biomass inserted into a process for the pretreatment of biomass.

The process for the treatment of biomass taken here as an example and represented in FIG. 1 comprises a first stage of impregnation of the biomass in a vertical reactor 3, followed by a stage of pretreatment of the biomass, once impregnated, in a horizontal steam explosion reactor 4.

These stages of the process are carried out continuously and are described in detail below using the description of the items of equipment used to implement it:

A vessel for preparation 1 of an impregnation liquor containing a chemical catalyst is provided, which liquor is formed from water E and from catalyst A which will feed it; the catalyst in this case is a strong acid of concentrated sulfuric acid type in an aqueous phase, this vessel making it possible to feed the impregnation reactor 3 with a mixture of water E and of chemical catalyst A, A conical screw 2 (also called plug screw or sealing screw) for feeding with fresh biomass (in this instance wheat straw P) into the impregnation reactor 3, A line for feeding the reactor with impregnation liquor connecting the vessel for preparation of liquor 1 and the impregnation reactor 3, An impregnation reactor 3 equipped with two upward transportation screws (not represented) making it possible for the biomass to pass from the impregnation zone in the lower part of the reactor to the draining zone in the upper part of the reactor, and to bring the impregnated and drained biomass to the reactor outlet located at the top of the reactor.

This impregnated and drained biomass is subsequently sent to the pretreatment by a feedline emerging in a second conical screw 2', This second conical screw 2' feeds a pretreatment reactor 4 with impregnated biomass, The pretreatment reactor 4 treats the impregnated biomass by steam explosion, A water circuit for washing the conical screws 2,2' of the impregnation reactor 3 and of the pretreatment reactor 4, represented symbolically in FIG. 1 by water inlets E at said screws, is provided, A means for separation of the steam 5 is fed by the reactor 4 with biomass which has undergone cooking by steam explosion, for example of cyclone type, with at the high outlet steam V and at the low outlet the pretreated/exploded biomass, also called must (or marc) M.

This must M exhibits at this stage a sufficient accessibility of the cellulose to enzymes to be treated by enzymatic hydrolysis for the production of 2G sugars. The conditions of the enzymatic hydrolysis and of the consecutive or simultaneous fermentation which follow this separation (not represented in FIG. 1) are suitable for the desired products and are known to a person skilled in the art.

The use of the pretreatment technique described above results in the deposition of different types of biomass (wheat straw here, but also miscanthus, poplar, and the like), which accumulate at/adhere to the surface of at least one of the transportation screws internal to the pretreatment reactor 4. These deposits undergo a cooking over times longer than the normal residence time of the biomass in the reactor, and are transformed into a residue, which can be called "coke" here. This "coke" can create various operating problems, such as blockages of the outlet orifice of the reactor 4 or an increase in the frictional actions of the transportation screw(s) in question on the wall of the chamber in which they are housed, and this may result in a reduction in the performance characteristics of the pretreatment unit in its entirety as represented in FIG. 1.

The definition of the composition of the "coke" has proven to be problematic because it concerns a residue, the appearance and the composition of which change over time: at the start of a production cycle, the material which is deposited is biomass; it thus has essentially the same characteristics as the biomass which continues its journey through the reactor 4 and toward the downstream stages. The deposit which is formed by adhesion to the internal wall of the reactor 4 will remain for a much longer time under the cooking conditions (temperature in particular) than desired. The effect of the temperature affects the composition and the morphology of the residue, which will change toward an increasingly "cooked" residue. The more the residue is "cooked", the more compact it is and the more it adheres to the walls of the reactor.

These "coke" deposits are cumulative: the longer the continuous operating time of the tool, the greater the amount of coke deposited, and the more the "layers" of coke close to the wall will change toward a very hard solid. These deposits thus bring about a fouling phenomenon, by increasing the thickness of the walls and by reducing the useful volume of the reactor. Depending on the configuration of the cooking reactor, and in particular the type of internal in place, there may be observed interference with the rotation of certain elements, such as the screw, or one at least of the screws for transportation of the biomass in the reactor being cooked. This interference is observed in particular by an increase in the power of the motor rotating the screw.

Throughout the production, it can also happen that a part of this residue, which is more or less hardened, detaches from the wall of the reactor, under the effect, for example, of the rotation of the screw or of one at least of the transportation screws internal to the reactor or of the passage of the biomass through the reactor: thus, particles with a much greater density than the bed of biomass being cooked can be caused to detach and to be entrained toward the outlet orifice of the reactor, which can generate blockages or operating problems downstream. Despite these detachments, it is found that the deposits continue to increase over time during a given production cycle.

After stopping, cooling and opening the cooking reactor 4, it could be found that the coke exists in two forms: a hard form in direct contact with the internal walls of the reactor and a more friable form which covers the hard coke. The difference between these two cokes is found in their elemental compositions, as shown in table 1 below.

|  | Friable coke | Hard coke |
|---|---|---|
| Carbon content (%) | 44.57 | 65.07 |
| Hydrogen content (%) | 5.85 | 4.67 |
| Oxygen content (%) | 34.63 | 24.58 |

It is observed that the percentage of carbon contained in hard coke is higher than that in friable coke, while an opposite trend is noted for the oxygen content, and similar values are noted for the hydrogen content. It emerges from this that friable coke is, as it were, the precursor of dense coke.

The invention consists in continuing the operation of the two impregnation 3 and pretreatment 4 reactors, while carrying out the chemical cleaning of the reactor 4 in order to extract this coke C and/or to slow down its formation.

This cleaning does not require the opening of the reactor and the mechanical cleaning of the interior of the reactor, as was the case previously. This cleaning according to the invention, described in detail below, is thus faster, more economical and safer, since it makes it possible to limit the operating risks associated with the assembling and dismantling of the unit and, above all, since it makes it possible not to stop the production.

An example of implementation of the process according to the invention and its alternative forms are explained with the help of the combined figures. It requires the following additional items of equipment, with respect to those already described, in the light of FIG. 1:

A vessel for preparation 6 of a cleaning liquor EB containing a base. This vessel 6 makes it possible to feed the pretreatment reactor 4 with basic solution at a certain concentration. It is fed with water E and with base B (for example a base B in the form of a concentrated aqueous KOH solution), the contribution of which is adjusted in order to obtain a liquor in the desired amount and at the desired concentration of base/pH.

A line for feeding the reactor 4 with cleaning liquor connecting the vessel for preparation of cleaning liquor 6 and the pretreatment reactor 4 to be cleaned, if appropriate preheating it by ad hoc items of equipment (heating resistors surrounding the pipes, for example), with items of equipment suitable for injecting the cleaning liquor into the reactor 4 under pressure, An inlet for rinsing water ER for the cyclone 5.

The course of the implementational example of the cleaning process according to the invention comprises two consecutive sequences:

Sequence 1: Injection of the preheated basic liquor EB into the reactor 4 while the reactor is being fed with the acidic biomass.

The injection conditions are as follows:

the basic solution EB is an aqueous KOH solution, with a KOH concentration of 1% to 50% by weight of KOH, preferably from 5% to 12% by weight of KOH, with respect to the water the flow rate of the solution EB into the reactor is between 100 and 500 kg/h, in particular approximately 300 kg/h the degree of filling by the biomass impregnated with the basic solution EB of the reactor 4 is from 20% to 90%, in particular approximately 30% the temperature at which the solution EB is injected into the reactor 4 is between 80° C. and 200° C., in particular approximately 130° C.

the temperature of the reactor 4 is between 150° C. and 220° C., in particular approximately 200° C.

the duration of this sequence is between 15 minutes and 8 hours; it is in particular 2 hours the residence time of the solution EB in the reactor 4 is between 5 and 15 minutes, and in particular approximately 10 minutes.

Sequence 2: Cleaning the cyclone 5 by rinsing with the water ER to complete the cleaning. The term "water flush" can be used, insofar as the rinsing consists, in this implementational example, in spraying water under pressure into the cyclone, which water is subsequently rapidly discharged.

The operating conditions for this sequence are as follows:

number of rinsing operations: from 1 to 10, for example equal to 2 temperature of the rinsing water: 20° C. to 80° C., for example 20° C. (i.e. either a temperature at ambient or close to ambient, or a higher temperature requiring preheating of the rinsing water ER)

In the cleaning phase, a must is obtained at the outlet of the cyclone 5 which is no longer the conventional acidic must M but a basic must M1.

The frequency of the cleaning procedure can vary widely depending on the type and size of the pretreatment reactor 4, on the type of biomass being treated, and the like. For example, the cleaning can be triggered when the torque of one of the transportation screws internal to the reactor increases by more than 15%, with respect to the torque observed at the start of production. It can also be triggered after a given period, which can range from 2 hours to 4 months of production.

Different alternative forms can be introduced to the example of cleaning process described above, while remaining within the scope of the invention, some of which are described in detail below (some at least of these alternative forms can be alternative or cumulative):

A—During cleaning, the concentration of acid A of the vessel for preparation 1 of the impregnation liquor can be reduced to a zero concentration optionally, that is, ultimately, an impregnation which is carried out only with water.

Figure 2:
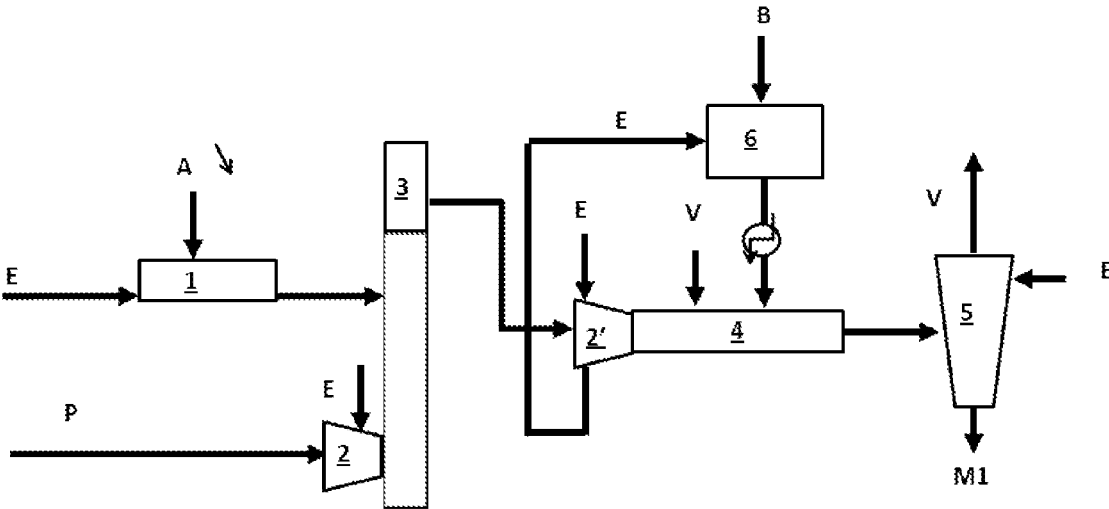
FIG. 2 represents a first alternative form of the process according to FIG. 1.

B—The aqueous washing liquor E for the screw 2' (which is neutral) bringing the impregnated biomass into the reactor 4 can be recycled into the vessel for preparation 6 of the basic solution EB during the cleaning, which makes it possible to reduce the additional water consumption due to the cleaning, as represented in FIG. 2.

C—The biomass can be impregnated with a basic liquor during the cleaning sequence, either with the same basic liquor EB as that prepared in the vessel 6 or a different basic liquor, in particular in terms of concentration of base B. This alternative form makes it possible to reduce the amount of pure basic solution to be introduced into the pretreatment reactor 4, since there will no longer be, or will be less, acid to be neutralized in order to reach the targeted basic pH. However, a certain amount of basic liquor will be removed in the pressate (which corresponds to the water extracted from the screw 2').

Thus, it may still be necessary to top up with basic liquor EB directly in the reactor 4 (via the vessel 6).

Figure 3:
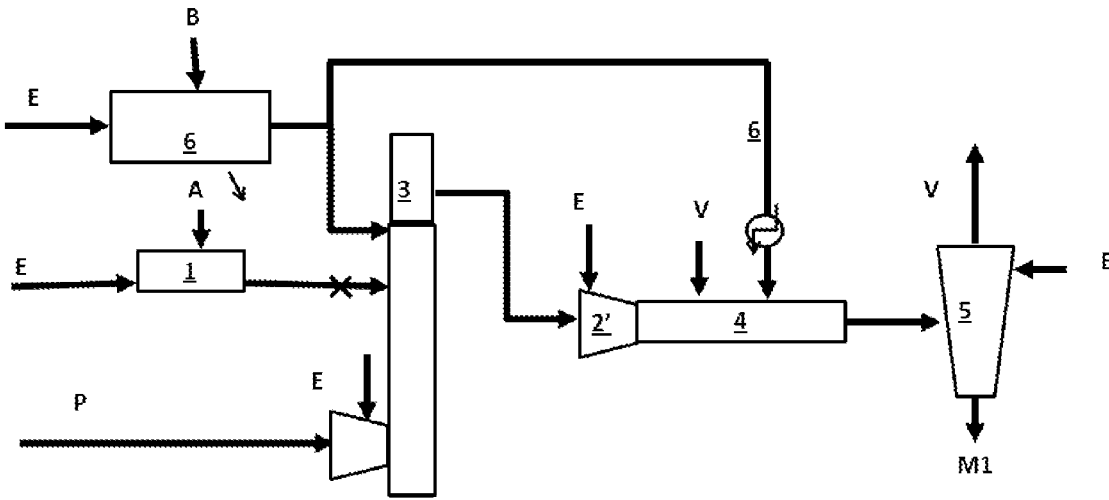
FIG. 3 represents a second alternative form of the process according to FIG. 1.

FIG. 3 illustrates this alternative form: the vessel 6 for preparation of basic liquor EB still has two inlets, one for the concentrated base B (concentrated KOH), the other for the water, but here it also has two outlets: one outlet to the pretreatment reactor, as above, and one outlet to the impregnation reactor 3. With this configuration, it is possible to feed the impregnation reactor 3 either with the acid solution EA from the vessel 1 in production mode or with the basic solution EB from the vessel 6 in production+cleaning mode.

The vessel 6 can thus simultaneously feed the two reactors 3 and 4, or at least for a common period during the cleaning of the reactor 4. It is also possible to anticipate and begin to feed one of the reactors with basic solution EB before the other, in particular the impregnation reactor 3 before the start of cleaning by the solution EB of the pretreatment reactor 4.

Figure 4:
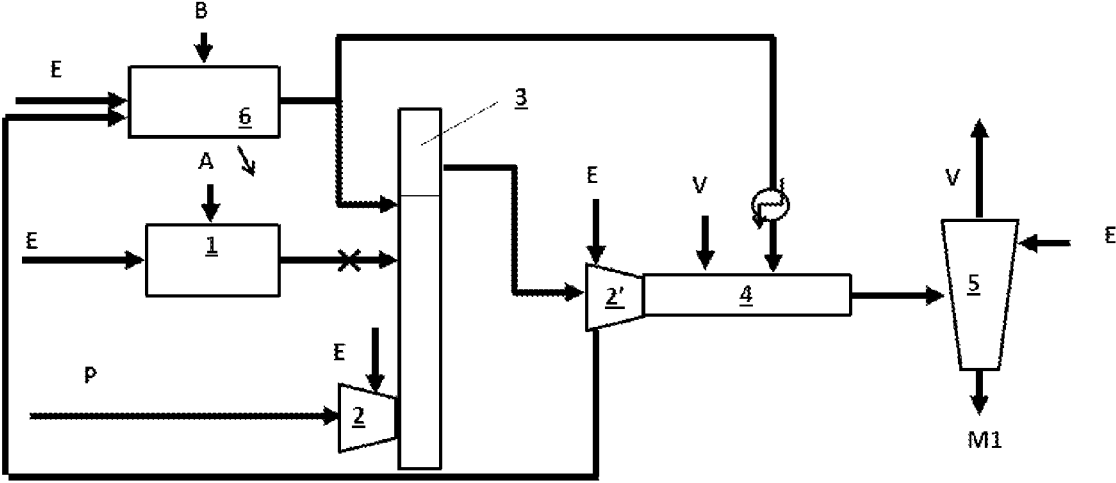
FIG. 4 represents a third alternative form of the process according to FIG. 1.

D—It is also possible to combine the two preceding alternative forms, as represented in FIG. 4, with, at the same time, the recycling of the (basic) pressate at the outlet of the screw 2' in the vessel 6 for preparation of basic liquor EB, and the feeding by this same vessel 6 of the two reactors 3 and 4 during at least a part of the cleaning. The impregnation of the biomass, during the cleaning, is carried out with basic liquor by changing the impregnation reactor during the cleaning.

Figure 5:
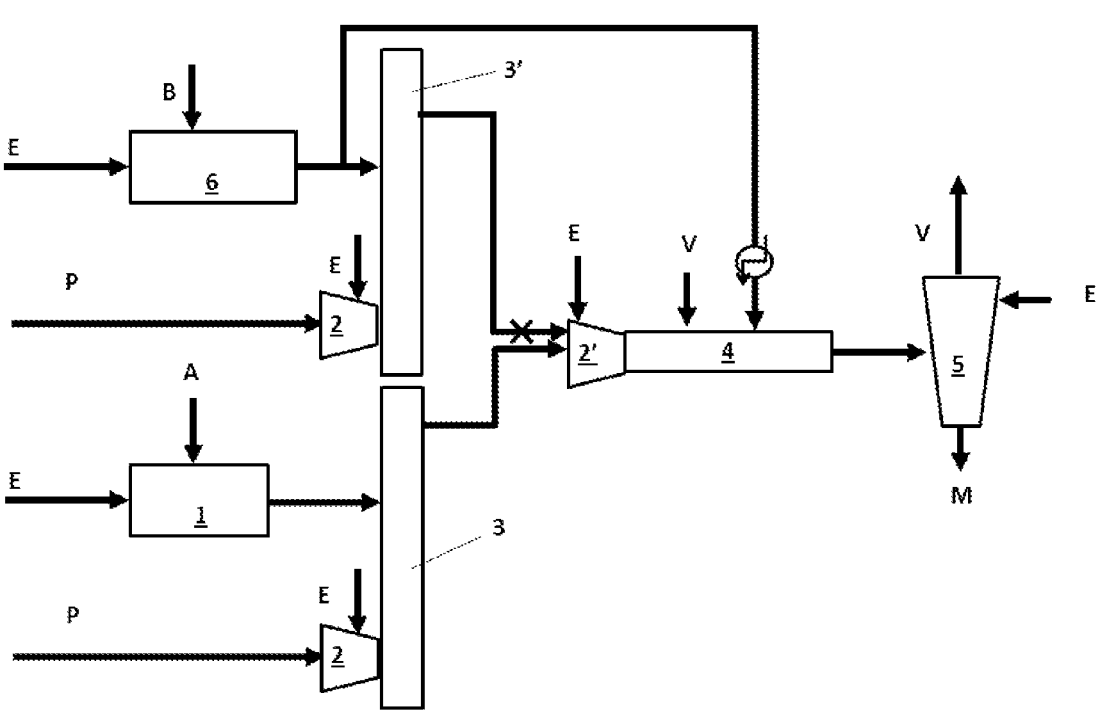
FIG. 5 represents a fourth alternative form of the process according to FIG. 1.

E—It is also possible to use two impregnation reactors 3,3' operating alternately, as represented in FIG. 5. As in the alternative form C, the biomass is impregnated not with an acidic liquor EA but with a basic liquor EB during at least a part of the cleaning of the reactor, indeed even also a little before, in the following way: in production mode, the biomass is brought into the pretreatment reactor 3 fed with acidic liquor by the vessel 2, and in production+cleaning mode (during all or part of the cleaning), the biomass is rerouted to the impregnator 3', which itself is fed with basic liquor EB from the vessel 6. A second dedicated impregnation reactor 3' is thus used for the cleaning. This embodiment exhibits the advantage, in comparison with the alternative form C, of reducing the transition times between acidic impregnations and basic impregnations.

F—The alternative forms E and B can be combined, that is to say the two impregnation reactors 3,3' can be used and the water extracted from the screw 2' can be recycled in the vessel 6 for preparation of basic liquor EB.

Figure 6:
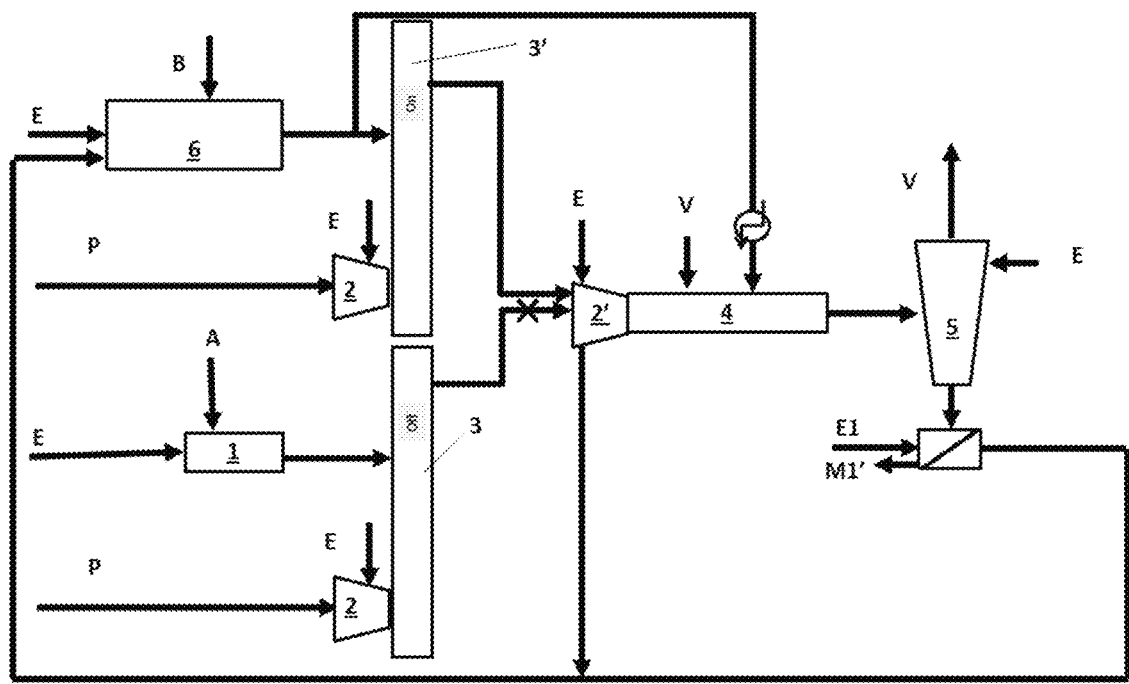
FIG. 6 represents a fifth alternative form of the process according to FIG. 1.

G—The must (also called marc) can be recycled, in particular in the context of the alternative form E having two impregnation reactors: the basic pretreated biomass M1 which exits from the separation device 5 during the cleaning of the pretreatment reactor 4. This is because, during this period, it is basic. It is then possible to wash this must M1 at the outlet of the separation device 5 with water: it becomes a washed basic must M1', as represented in FIG. 6; and to extract a basic aqueous phase E1 therefrom which is recycled in the vessel 6 for preparation of the basic liquor. The impregnation, during the cleaning, is carried out with a basic liquor by changing the impregnation reactor and the vessel for preparation of liquor.

Figure 7:
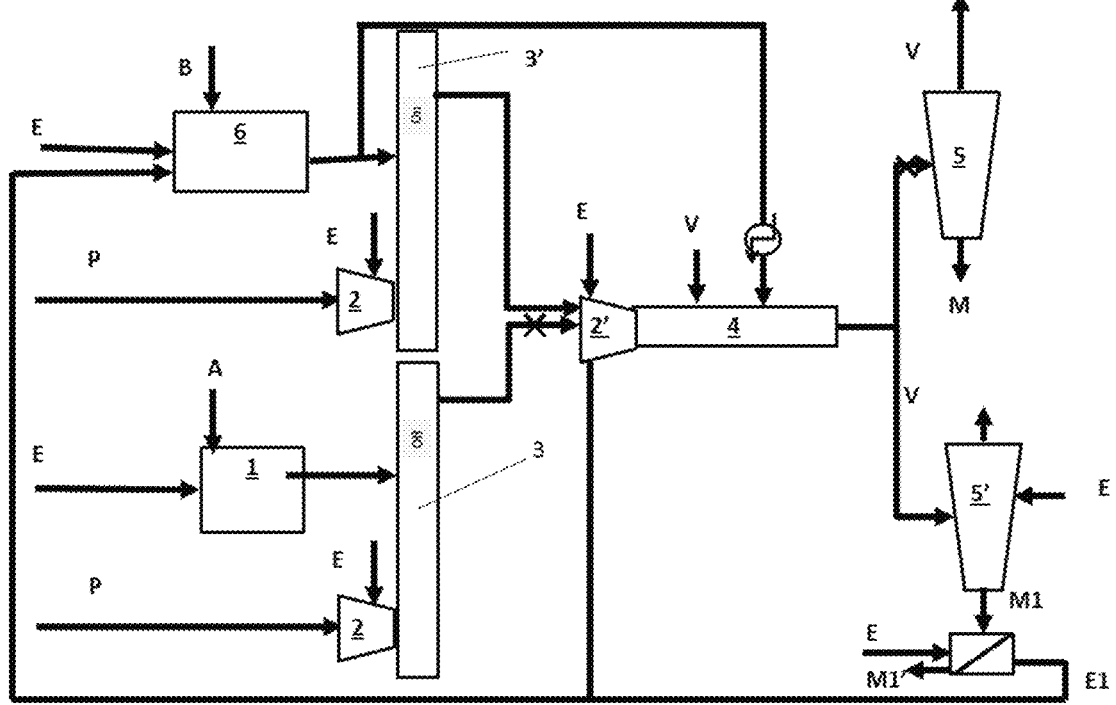
FIG. 7 represents a sixth alternative form of the process according to FIG. 1.

H—Another alternative form consists in using two separation devices 5,5' (cyclone) operating alternately, as represented in FIG. 7: a cyclone 5' is added which is dedicated to the treatment of the basic marc M1. In production mode, the cyclone 5 is operational; it treats an acidic marc M1. In production+cleaning mode, the output of the reactor 4 is switched to the second cyclone 5', which will thus separate only basic marc M1. The advantage of this alternative form is to reduce the transition time between the two modes. FIG. 7 combines this alternative form with the alternative form G: the basic marc, once separated in the cyclone 5', is also washed in order to recycle the basic aqueous washing liquor E1 to the vessel for preparation 6 of basic liquor.

Figure 8:
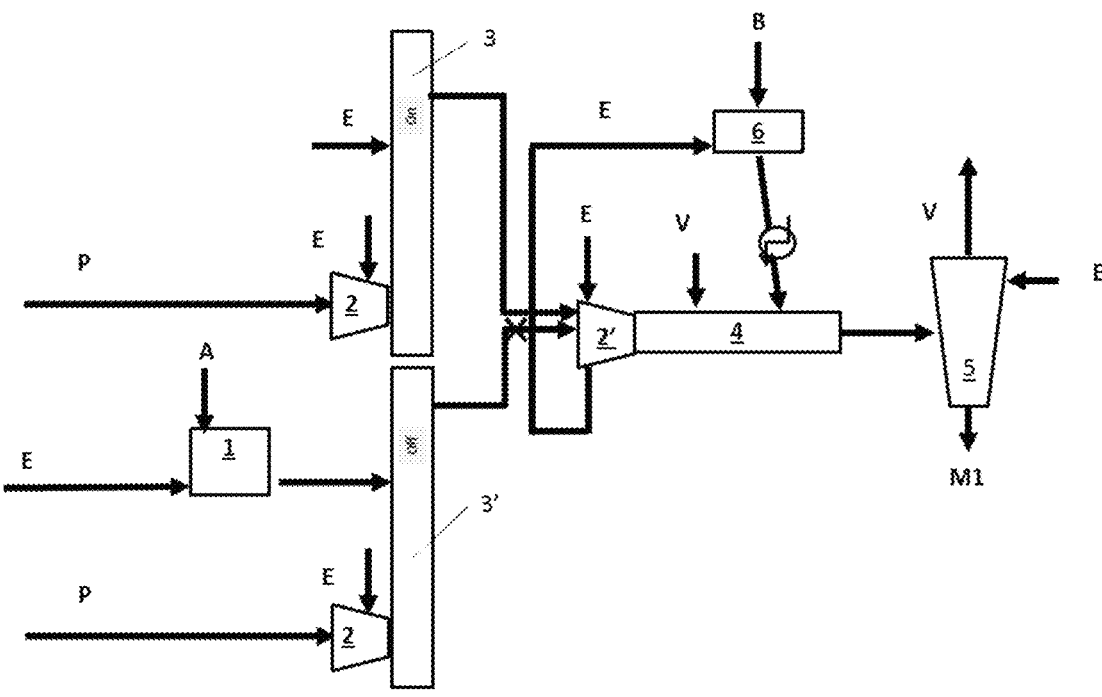
FIG. 8 represents a seventh alternative form of the process according to FIG. 1.

J—This alternative form emerges from the preceding alternative form E having two impregnation reactors 3,3', with the following difference: In production mode, use is made of the conventional impregnation reactor 3 fed with acidic solution EA by the vessel 1. In production+cleaning mode, the system is switched here to the second impregnation reactor 3' which is fed only with water, as represented in FIG. 8: during the cleaning, the biomass is thus impregnated only with an aqueous solution at neutral pH (and not a basic solution EB).

Figure 9:
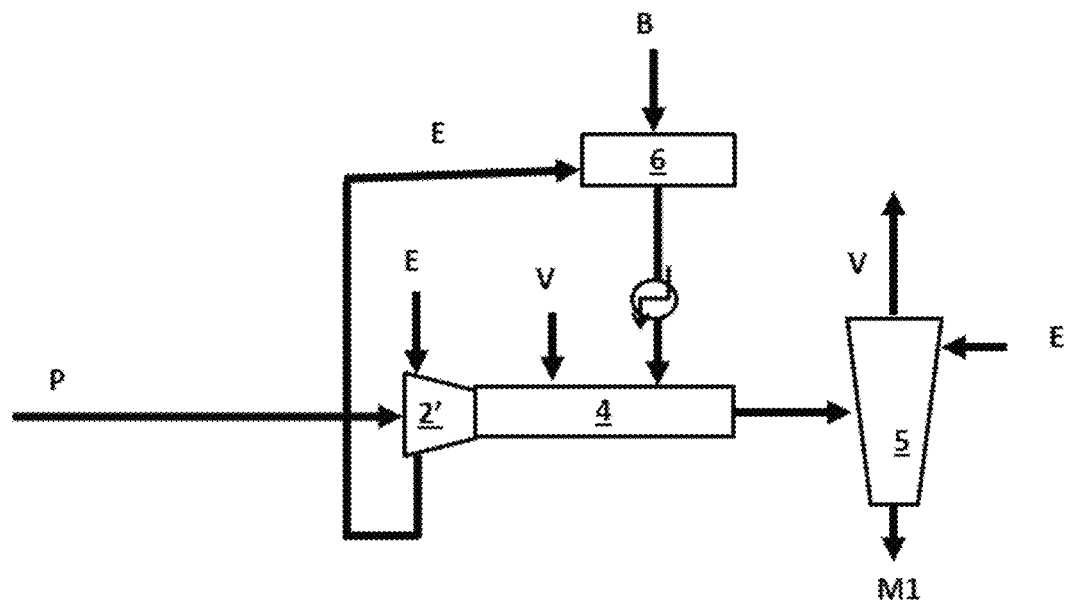
FIG. 9 represents an eighth alternative form of the process according to FIG. 1.

K—The invention also applies to processes for the pretreatment of biomass without prior preimpregnation with a liquor (reference is then made to self-hydrolysis): in this case, the biomass P, after having optionally undergone a treatment of mechanical (grinding, and the like), thermal (drying) or humidification type, is introduced directly into the pretreatment reactor 4, as represented in FIG. 9.

Figure 10:
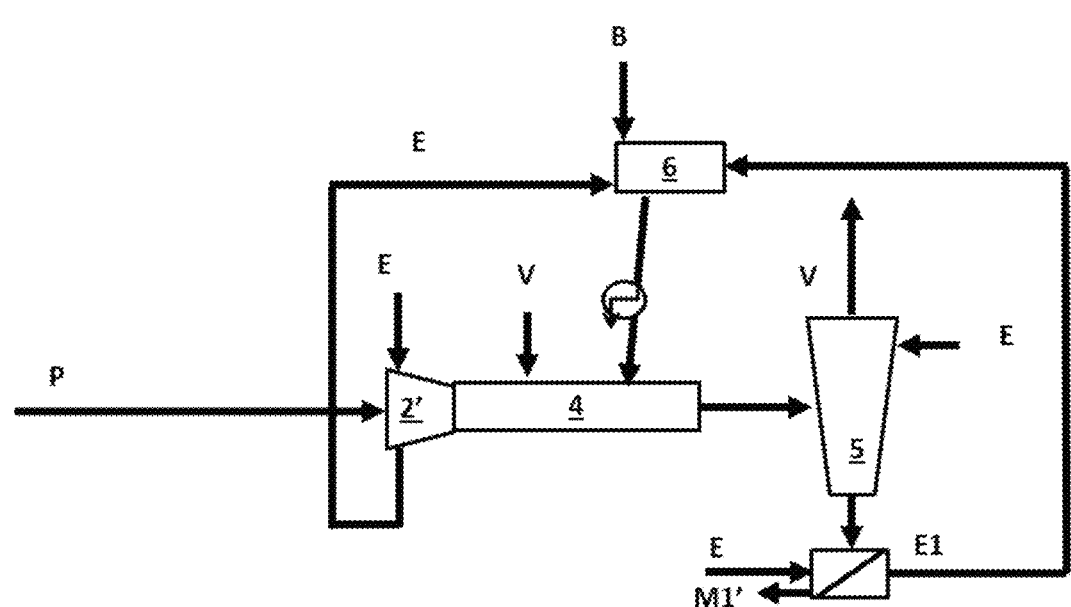
FIG. 10 represents a ninth alternative form of the process according to FIG. 1.

L—This alternative form, illustrated in FIG. 10, combines the recycling of the pressate E1 of the alternative form E with that of the aqueous washing liquor for the screw 2' of the alternative form B to the vessel 6 for preparation of the basic liquor EB. Both the consumption of water and of base required for the cleaning according to the invention are thus more substantially reduced.

Figure 11:
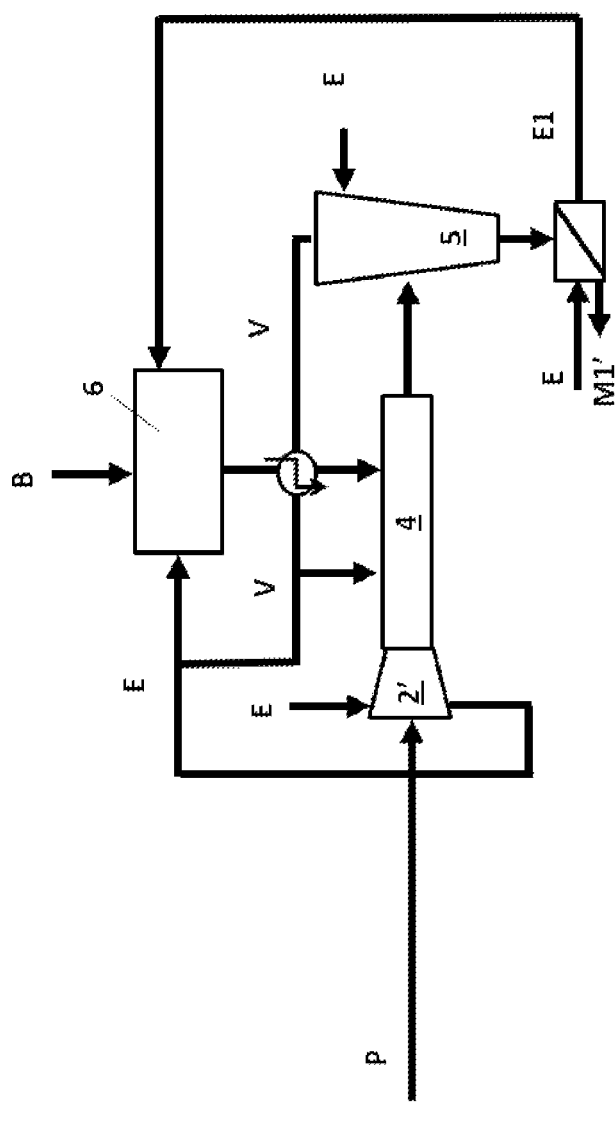
FIG. 11 represents a tenth alternative form of the process according to FIG. 1.

M—This alternative form, represented in FIG. 11, recommends a thermal integration of the process, by condensation of the steam V at the outlet of the cyclone 5. This steam V is used to heat the basic liquor EB circulating in pipes between the vessel 6 and the pretreatment reactor 4 via a heat exchanger (not represented). It is also used to reduce the amount of water used in the vessel 6 by recovering the condensate resulting from the cooling of the steam exiting from the cyclone, via a condenser (not represented).

N—According to another alternative form, it is possible to choose to inject biomass impregnated with acidic liquor EA into the pretreatment reactor 4 from the impregnation reactor 3 in production mode, and to directly inject the nonimpregnated biomass P into the pretreatment reactor 4 in production+cleaning mode, by then stopping the feeding of biomass impregnated with acidic liquor.

O—According to yet another alternative form, which can be combined with all the others, it is possible to choose to inject, into the pretreatment reactor, a given impregnated biomass in production mode and to inject another biomass, impregnated or not with a liquor, in production+cleaning mode. For example, in production, a straw-type biomass is chosen and, in production+cleaning mode, a more abrasive poplar-based biomass is chosen: a temporary increase is thus brought about in the cleaning time, the abrasive nature of the biomass, in order to help to more easily detach solid coke residues from the walls.

EXAMPLES

Example 1 not in Accordance with the Invention

It uses the configuration presented in FIG. 1, without the addition of the vessel for preparation of a basic aqueous liquor (KOH) specific to the invention.

It concerns a mechanical cleaning of the pretreatment reactor with stopping of the production and opening of the reactor, according to an earlier solution.

It was carried out with wheat straw as biomass. The characteristics and composition of the feedstock are as follows:

Solids content: 91.07%

Biomass flow rate: 65 kg SC/h

The operating conditions for producing pretreated biomass are as follows:

Impregnation for the production in the impregnation reactor 3:

Acidic $H_2SO_4$ solution flow rate: 1.5 kg/h (pH of approximately 1)

Steam explosion of the impregnated biomass in the pretreatment reactor 4:

Residence time: 5 min

Production duration: 72 hours

Mechanical cleaning according to prior art:

Temperature drop time: 48 hours

Opening and dismantling time: 8 hours

Cleaning time: 8 hours

Time for reassembling the reactor: 8 hours

The weight of coke C produced is 16 kg occupying a volume of 0.012 $m^3$ in the reactor 4, i.e. a reduction in the reactor volume of 8.7% and a coke production throughput of 222 g/h.

Example 2 in Accordance with the Invention

It uses the configuration presented in FIG. 1, with the addition of the vessel for preparation of a basic aqueous liquor (KOH) specific to the invention.

The characteristics and composition of the wheat straw feedstock are identical to those of the wheat straw used in example 1.

The operating conditions are described in detail below:

Mode 1=production:

Impregnation for the production in the impregnation reactor 3:

Acidic solution flow rate: 1.5 kg/h ($H_2SO_4$)

Steam explosion of the impregnated biomass in the pretreatment reactor 4:

Residence time: 5 min

Production duration: 20 hours

The pressate E1 resulting from the screw 2' is completely recycled to the vessel 1 for preparation of the acidic aqueous solution.

After 20 hours of production, the cleaning sequence is carried out under the following conditions:

Mode 2=production+cleaning:

Impregnation in the impregnation reactor 3:

Acidic solution flow rate (acidic solution EA): 1.5 kg/h ($H_2SO_4$)

Steam explosion of the impregnated biomass in the pre-treatment reactor 4:

Residence time: 10 min

Temperature in the reactor: 200° C.

KOH flow rate: sufficient to lower the SC down to the saturation value of the biomass Duration of the cleaning: 2 hours Concentration of KOH in the liquor: sufficient to change the biomass from a pH of 3 to a pH of 13

Number of cycles: 3 cycles of mode 1 (production) and of mode 2 (production+cleaning)

Cleaning of the cyclone 5 (separation device)

Number of water flushes: 2, after each cleaning operation

After 3 cycles of mode 1+mode 2, for a total production duration of 66 h (60 hours of production and 6 hours of cleaning), the cleaning proved to be effective.

This is because the weight of coke C recovered at the end of the procedure (thus after these 3 cycles) does not exceed 3 kg, i.e. a coke production throughput of 39 g/h.

Thus, the cleaning procedure made it possible to reduce the production throughput from 222 g/h in 72 hours to only 39 g/h after a production of 60 h separated from 3 cleaning operations each of 2 hours.

Example 3 in Accordance with the Invention

It is identical to example 2 except that the production does not last 20 hours but 80 hours. After 3 production and cleaning cycles for a total operating time of 246 hours (240 hours of production mode and 6 hours of production+cleaning mode), the cleaning proved to be effective.

This is because the weight of coke C recovered at the end of these three cycles does not exceed 3 kg, i.e. a coke production throughput of 41 g/h.

Thus, the cleaning procedure made it possible to reduce the production throughput from 222 g/h in 72 h to only 41 g/h after a production of 240 hours separated from 3 cleaning operations each of 2 hours.

Example 4 in Accordance with the Invention

The feedstock is still wheat straw, the characteristics and composition of which are as follows:

Solids content: 88.30% by weight

Biomass flow rate: 65 kg SC/h

The operating conditions are described in detail below:

Mode 1=production:

Impregnation for the production in the impregnation reactor 3:

Acidic solution flow rate: 1.5 kg/h

Steam explosion of the impregnated biomass in the pre-treatment reactor 4:

Residence time: 5 min

Production duration: 80 hours

After 80 hours of production, the cleaning sequence is set in motion under the following conditions:

Mode 2=production+cleaning:

Impregnation in the impregnation reactor 3:

Acidic solution flow rate: 1.5 kg/h

Steam explosion of the impregnated biomass in the pre-treatment reactor 4:

Residence time: 10 min

Temperature of the reactor: 200° C.

KOH flow rate: sufficient to lower the SC down to the saturation value of the biomass Duration of the cleaning: 2 h Concentration of the KOH in the liquor: sufficient to change the biomass from a pH of 3 to a pH of 13

Number of cycles: 8 cycles of mode 1 (production) and of mode 2 (production+cleaning)

Cleaning of the cyclone 5

Number of water flushes: 2

After these 8 cycles, for a total operating time of 656 hours (640 hours of production and 16 hours of production+cleaning), the cleaning proved to be effective.

This is because, in total, 14.96 kg of coke C were recovered, i.e. a coke production throughput of 22 g/h.

Example 5 in Accordance with the Invention

It was carried out with SRC poplar wood, the characteristics and composition of which are as follows, with the configuration of FIG. 1 with addition of the vessel 6 for preparation of basic liquor, as for example 2:

Solids content: 55.50% by weight

Biomass flow rate: 80 kg SC/h

Mode 1=production:

Impregnation for the production in the impregnation reactor 3:

Acidic solution (2.5% by weight) flow rate: 2.7 kg/h

Steam explosion of the impregnated biomass in the pre-treatment reactor 4:

Residence time: 7.5 min

Production duration: 60 hours

After 60 hours of production, the cleaning sequence is set in motion under the following conditions:

Mode 2=production+cleaning:

Impregnation in the impregnation reactor 3:

Acidic solution (2.5% by weight) flow rate: 2.7 kg/h

Steam explosion of the impregnated biomass in the pre-treatment reactor 4:

Residence time: 7.5 min

Temperature of the reactor: 200° C.

KOH flow rate: sufficient to lower the SC down to the saturation value of the biomass Duration of the cleaning: 2 h Concentration of the KOH in the liquor: sufficient to change the biomass from a pH of 3 to a pH of 13

Number of cycles: 3 cycles of mode 1 and of mode 2

Cleaning of the cyclone 5

Number of water flushes: 2

After these 3 cycles, for a total operating time of 186 hours (180 hours of production and 6 hours of cleaning), the cleaning proved to be effective.

This is because, in total, 8 kg of coke were recovered, i.e. a coke production throughput of 121 g/h.

In conclusion, the cleaning according to the invention avoids having to stop the production, with all the disadvantages which are connected with this (loss of time, loss of yield, more burdensome servicing by operators), or, at the very least, makes it possible to very significantly space out the complete cleaning operations with stopping of production.

The invention claimed is:

1. A process for treatment of a lignocellulosic biomass (P), said process comprising:

impregnating the lignocellulosic biomass (P) with an acidic aqueous solution (EA) in an impregnation reactor (3) to form an impregnated lignocellulosic biomass (P), pretreating the impregnated lignocellulosic biomass (P) in a pretreatment reactor (4), and providing a phase of continuous cleaning of the pretreatment reactor (4) while pretreating the impregnated lignocellulosic biomass (P) in a pretreatment reactor (4), wherein the phase of continuous cleaning comprises:

introducing a basic aqueous solution (EB) into said pretreatment reactor (4) containing the impregnated lignocellulosic biomass (P), and adjusting a concentration of the basic aqueous solution (EB) to increase a pH of the impregnated lignocellulosic biomass (P) in the pretreatment reactor (4) from an acidic pH range of between 0.5 and 3, to a basic pH range of between 8 and 14, wherein the pH of the basic aqueous solution (EB) before introduction into the pretreatment reactor (4) is greater than or equal to 9.

2. The process as claimed in claim 1, wherein the basic aqueous solution (EB) is heated before introduction into the pretreatment reactor (4) to a temperature of at least 40° C.

3. The process as claimed in claim 1, wherein the pretreatment reactor, has an internal volume and wherein the temperature of the internal volume of the pretreatment reactor is at least 120° C. when the basic aqueous solution is introduced.

4. The process as claimed in claim 1, wherein the introduction of the basic aqueous solution (EB) into said pretreatment reactor (4) containing the impregnated lignocellulosic biomass (P) has a duration of between 15 minutes and 8 hours.

5. The process as claimed in claim 1, wherein during the phase of continuous cleaning of the pretreatment reactor (4), the basic aqueous solution (EB) has a residence time in said pretreatment reactor (4) of between 5 and 15 minutes.

6. The process as claimed in claim 1, wherein during the phase of continuous cleaning of the pretreatment reactor (4), the basic aqueous solution (EB) is introduced at an inlet of said pretreatment reactor (4) at flow rate, the process as claimed in claim 1, further comprises adjusting the flow rate so that a solids content SC of the lignocellulosic biomass (P) decreases during its passage through the pretreatment reactor from a value of 30% SC to 60% SC.

7. The process as claimed in claim 1 further comprising: introducing a change to at least one of a physical, chemical or rheological characteristic of the impregnated lignocellulosic biomass (P) in the pretreatment reactor (4) during the continuous cleaning phase.

8. The process as claimed in claim 1, wherein pretreating the impregnated lignocellulosic biomass (P) in a pretreatment reactor (4) is achieved by steam explosion cooking, wherein said steam explosion cooking provides steam having thermal energy in the pretreatment reactor (4), the process of claim 1 further comprising:

exhausting at least a first portion of the steam at an outlet of a separation device (5) is positioned at an outlet of the pretreatment reactor (4), recovering said thermal energy of the at least first portion of steam via a heat exchanger, and heating one of the basic aqueous solution (EB), an acidic aqueous solution (EA), or a neutral aqueous solution (E), and condensing a second portion of the steam via a condenser.

9. The process as claimed in claim 1, further comprising reducing or eliminating acid content of the acidic aqueous solution (EA).

10. The process as claimed in claim 1, wherein during the phase of continuous cleaning of the pretreatment reactor (4), the acidic aqueous solution (EA) is replaced by the basic aqueous solution (EB), or by an aqueous solution (E) having a neutral pH.

11. The process as claimed in claim 1, wherein the impregnation of the lignocellulosic biomass (P) is realized via a first impregnation reactor (3) and a second impregnation reactor (3') used in parallel, the first impregnation reactor (3) is fed with an acidic aqueous solution (EA) or with an aqueous solution (E) of neutral pH, and the second impregnation reactor (3') is fed with basic aqueous solution (EB), wherein the first impregnation reactor (3) and a second impregnation reactor (3') are operate alternately, and wherein the second reactor (3') is operational during the phase of continuous cleaning the pretreatment reactor (4).

12. The process as claimed in claim 1 further comprising:

separating the lignocellulosic biomass (P) and an aqueous phase in liquid or vapor form at an outlet of the pretreatment reactor (4) by a separation device (5), and wherein the phase of continuous cleaning of the pretreatment reactor (4) comprises, at least one rinsing of the separation device by an aqueous solution (E) after introduction of the basic aqueous solution (EB) into the pretreatment reactor (4).

* * * * *